United States Patent [19]

Perkins

[11] 4,014,971
[45] Mar. 29, 1977

[54] METHOD FOR MAKING A TYMPANIC MEMBRANE PROSTHESIS
[76] Inventor: Rodney C. Perkins, Palo Alto, Calif.
[22] Filed: May 11, 1973
[21] Appl. No.: 359,346
[52] U.S. Cl. .............................. 264/219; 264/222; 264/232; 264/330
[51] Int. Cl.$^2$ ........................................ B29C 23/00
[58] Field of Search .......... 264/222, 202, 212, 219, 264/232, 330; 3/1

[56] References Cited
UNITED STATES PATENTS

| | | | |
|---|---|---|---|
| 3,110,549 | 11/1963 | Cohen | 264/212 |
| 3,562,820 | 2/1971 | Braun | 3/1 |
| 3,587,586 | 6/1971 | Kronenthal | 3/1 |
| 3,722,003 | 3/1973 | Walchle | 3/1 |
| 3,823,423 | 7/1974 | Campo | 3/1 |
| 3,838,468 | 10/1974 | Armstrong | 3/1 |

*Primary Examiner*—Willard E. Hoag

[57] ABSTRACT

Synthetic anatomical members, such as a tympanic membrane and a malleus, are illustrated and a method for making them is disclosed. In accordance with the method, prepared collagenous tissue is placed in a mold and immersed in, or sprayed with, a buffered formaldehyde or functionally similar preservative. After removal from the mold, the tissue retains the shape assumed in the mold. Provisions are made for attaching other anatomical members, such as bone, to the tissue for use in, for example, en bloc reconstruction of an eardrum and ossicles.

3 Claims, 10 Drawing Figures

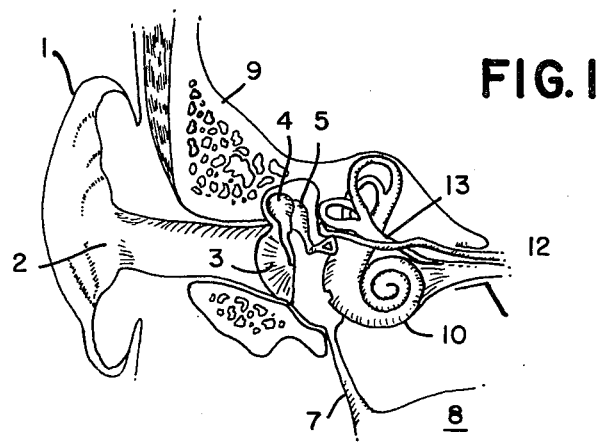
FIG. 1
FIG. 2
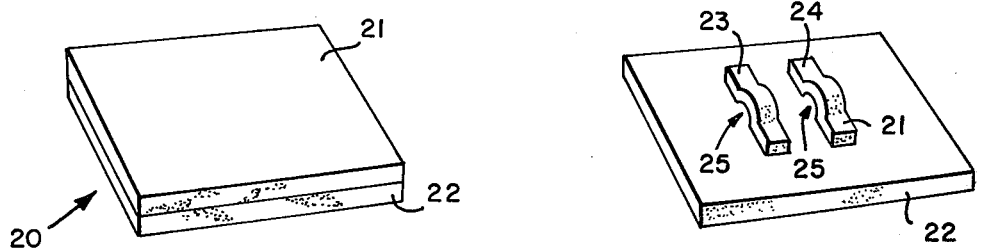
FIG. 3
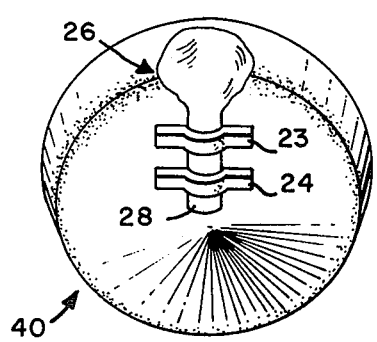
FIG. 7
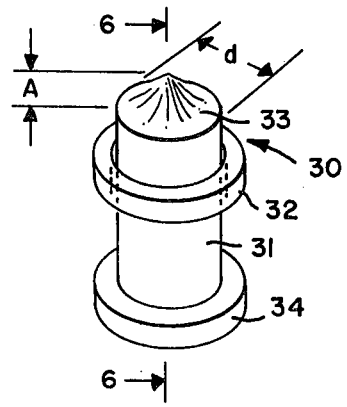
FIG. 4

METHOD FOR MAKING A TYMPANIC MEMBRANE PROSTHESIS

BACKGROUND OF THE INVENTION

The present invention relates, in general, to the shaping and forming of biological tissue for providing an implant for restoration of the structure and/or function of an anatomical member and, in particular, to a synthetic tympanic membrane, an associated malleus or ossicular substitute and method of making the same.

Over the past 20 years many methods and tissues have been used to repair tympanic membrane perforations. These efforts have generally utilized a scaffolding of autogenous connective tissue from various sources. The surface of epithelial covering has been derived from a free or pedicled skin graft or from epithelium migration from the host's external auditory canal skin. Dried (and, hence, nonviable) temporalis fascia in combination with epithelial migration from adjacent canal skin has been the most successful of this type of repair. Closure of the perforation is virtually assured with this technique but lateral displacement of the graft and blunting of the anterior sulcus has resulted in thick tympanic membranes in a small but significant percentage of cases. This undesirable effect frequently results in unsatisfactory hearing improvement when it occurs.

When, in addition, restoration of one or more of the ossicles is required, in particular, the malleus, some additional surgical difficulty is encountered. This is due to the lack of any provision in the conventional use of fascia tissue for preattaching a malleus or functionally similar member or for attachment of a host malleus to the tissue during surgery.

In addition, fascia tissue grafts do not ordinarily assume the conical shape of a natural tympanic membrane. This is undesirable in that the normal conical shape of the natural tympanic membrane is believed to be advantageous for better hearing.

More recently, the closure of tympanic membrane perforations and the reconstruction of ossicles with fresh sterile homograft tympanic membranes and ossicles has been attempted with varying degrees of success. In each case, temporal bone cores are taken at the time of an autopsy and dissected. The preparation of homograft tympanic membranes with or without the malleus and other ossicles involves delicate, time-consuming and expensive procedures which are wholly dependent on the availability of suitable donors.

The ready availability of an inexpensive synthetic tympanic membrane with or without one or more of the ossicles or functionally similar member and having the physical shape and characteristics of a homograft tympanic membrane is, therefore, highly desirable as is the availability of synthetic members for reconstructing other parts of the auditory system.

SUMMARY OF THE INVENTION

A principal object of the present invention is an apparatus and method for making synthetic anatomical members.

In accordance with this object, a principal feature of the present invention is a mold corresponding in size and shape to a desired anatomical member. A section of prepared collagenous tissue is placed on or in the mold and is treated as by applying a fixative thereto for causing the tissue to retain the shape of the mold.

In making a synthetic tympanic membrane, the preparation of the collagenous tissue involves, in the case of brain covering tissue, separating the thicker dura mater from the thinner arachnoid dura. One or more straps of dura mater are left attached to the arachnoid dura for forming one or more slings for receiving a host or synthetic malleus. A section of the arachnoid dura including the straps is then placed on the mold. The assemblage is then sprayed with or immersed in buffered formaldehyde or other functionally similar preservative.

Another feature of the present invention is the use of collagenous tissue for forming tissue molds within which living autogenous bone fragments are placed during surgery for reconstruction of bony anatomical members.

The availability of collagenous tissue far exceeds the availability of homograft tympanic membranes and is in general much easier to obtain. For example, a supply of tissue from a single autopsy provides sufficient tissue for making as many as twenty synthetic tympanic membranes. Furthermore, it is believed, collagenous tissue from animal sources other than humans may also be used. This would avoid entirely the problems associated with obtaining tissue from human donors.

These and other objects, features and avantages of the present invention will be apparent from the following detailed description and accompanying drawings.

DESCRIPTION OF THE DRAWINGS

FIG. 1 is a diagrammatic representation of the human ear.

FIG. 2 is a diagrammatic representation of a section of collagenous tissue.

FIGS. 3 and 9 are diagrammatic representations of a section of collagenous tissue prepared in accordance with the present invention.

FIGS. 4 and 5 are perspective views of molds in accordance with the present invention.

FIG. 7 is a perspective view of a synthetic tympanic membrane with a natural malleus in situ made in accordance with the present invention.

DETAILED DESCRIPTION

Figure 6:
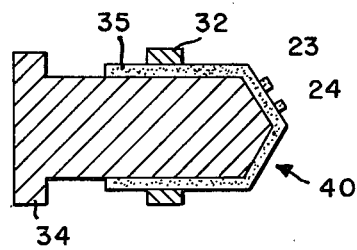
FIG. 6 is a cross-sectional view taken in the direction of lines 6—6 of FIG. 4.

Referring to FIG. 1, the ear can be divided into three portions: an outer ear, a middle ear, and an inner ear.

The outer ear is made up of an auricle 1 — that part external to the head — and an external ear canal 2.

The middle ear is separated from the outer ear by a thin conically-shaped tympanic membrane (the eardrum) 3. The middle ear is composed of the tympanic membrane 3 and the ossicles, Three little ear bones — the malleus (hammer) 4, the incus (anvil) 5, and the stapes (stirrup) 6. The air space surrounding these little bones is known as the middle ear space. This space is normally filled with air which passes through the Eustachian tube 7 from the throat 8 to the middle ear. Immediately behind the middle ear space is a bony honeycomb of air pockets called the mastoid.

The third portion, the inner ear, is composed of two segments: a cochlea (the hearing canal) 10 and a labyrinth (balance canals) 11. Both are normally filled with a watery solution which bathes the delicate nerve endings of a hearing and balance nerve, 12 and 13, respectively.

The structure and/or function of various ones of the above described parts of the ear, such as the tympanic membrane, ossicles and posterior ear canal wall may be restored individually or en bloc, if necessary, using synthetic anatomical members made in accordance with the present invention. The synthetic members, comprising collagenous tissue, as hereinafter described, serve as a scaffolding over which natural tissue growth occurs. Also the characteristics of the members and the method of fabricating them serve to provide the maximum possible restoration of function.

Referring to FIG. 2, in the fabrication of a synthetic tympanic membrane there is provided a section of collagenous tissue 20. Tissue 20 is typically brain covering tissue comprising a layer of dura mater 21 on a layer of arachnoid dura 22. However, other tissue from other parts of the human anatomy, as well as, it is believed, from other animals, may also be used. This is because tissue rejection does not appear to be a problem with homograft tympanic membranes; and synthetic membranes, as with the homografts, serve as a scaffolding over which natural tissue growth occurs within a relatively short period of time.

Referring to FIG. 3, in the initial preparation of tissue 20, the dura mater layer 21 is separated from the arachnoid dura layer 22 except for a pair of straps 23 and 24. A medial portion of each of straps 23 and 24 is thereafter elevated off the arachnoid dura for forming a receiving space 25 between the straps and the arachnoid dura layer. Alternatively, as shown in FIG. 9, a medial portion of a remnant layer of dura mater 21 may be elevated off the arachnoid dura layer 22 to form a pouch 37. The space 25 and pouch 37 are provided for receiving a bone member or malleus as hereinafter described with respect to FIGS. 7 and 8. As a further alternative, slits may be provided in dura layer 22 for receiving the bone member or malleus in lieu of both straps 23 and 24 and pouch 37. After the initial preparation, the tissue is formed with a mold into a shape corresponding to a natural tympanic membrane.

Referring to FIG. 4, there is provided a mold 30 comprising a cylindrically shaped shaft 31, whch approximates the size and shape of a human external ear canal. One end of shaft 31 is provided with a surface 33 corresponding to the shape of a natural tympanic membrane and a second end of shaft 31 is provided with a base 34.

After being prepared as described with respect to FIGS. 3 and 9, a section of arachnoid dura including straps 23 and 24 or pouch 37 is placed over the surface 33 of mold 30. An annular retaining sleeve 32 is then fitted over the tissue for holding the tissue on the mold. The base 34 serves as a means for holding the mold when placing the sleeve 32. Sleeve 32, however, may take other forms, such as a rubber O-ring or a female sleeve corresponding in size and shape to shaft 31. Alternatively, the tissue may be held in place on the mold simply by the fingers of the operator preparatory to fixing for shaping said tissue thereon.

The assemblage of the mold 30 and tissue 22 is then air dried, if desired, and immersed in a container of or sprayed with an agent, such as buffered formaldehyde or other functionally similar fixative such as gluteraldehyde, which causes the tissue to retain the configuration of the mold. Air drying is optionally used as it results in a thinning of the tissue, which may be desirable in some cases.

A suitable solution for fixing the tissue is 4% formaldehyde buffered to a pH of 5–7.0, although the percentage and pH are not critical to the invention. The tissue remains exposed to the fixative solution until adequate fixation has occurred rendering the new shape to be that of the mold. The tissue is then removed from the mold and stored. The storage solution has typically been ½% buffered formaldehyde at pH 7.0 but other solutions that maintain sterility could be used. When any bone tissue is incorporated as part of the desired end product, it is necessary to use a solution that will not cause decalcification. For this reason, the above solution of pH 7.0 has been used.

Figure 8:
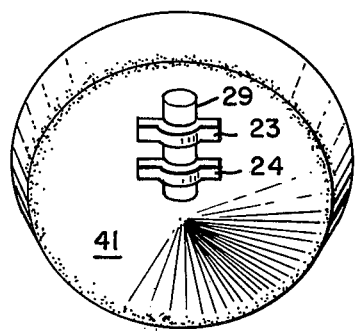
FIG. 8 is a perspective view of a synthetic tympanic membrane and a synthetic malleus made in accordance with the present invention.
Figure 9:
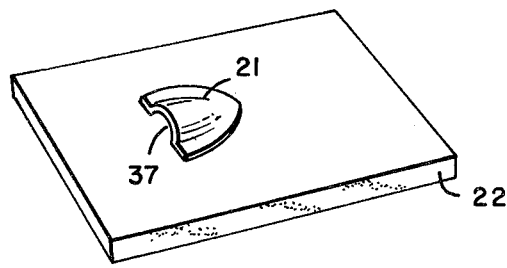

In FIGS. 6–8, there is illustrated a synthetic tympanic membrane 40 made in accordance with the above procedure. Membrane 40 has a generally conically shaped first wall 41 corresponding in size and shape to a natural tympanic membrane and a generally cylindrically shaped second wall forming a skirt 35 with a shape similar to that of the medial portion of the external ear canal. The skirt 35, which may be trimmed to suit a particular patient, serves to facilitate surgical implantation by providing a ready means for interfacing with host tissue.

Figure 10:
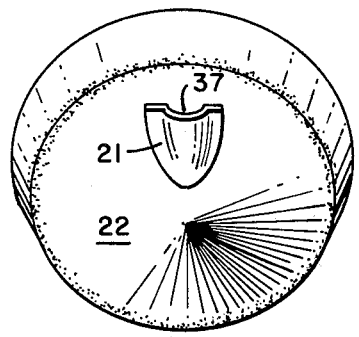
FIG. 10 is a perspective view of a synthetic tympanic membrane having a pouch for receiving a malleus in accordance with the present invention.

A natural malleus, indicated generally as 26 in FIG. 7, comprises a head 27 and a shank 28. If restoration of a malleus is not required by a patient, the straps 23 and 24 of the synthetic tympanic membrane 40 are slipped over the shank 28 of the malleus of the patient and the skirt 35 implanted in a conventional manner. In this regard, the adjacent ear canal tissue is elevated and placed over the skirt 35 to facilitate tissue migration onto the membrane. Alternatively, the patient's malleus may be inserted in the pouch 37 of FIG. 10. As a further alternative, it should be appreciated that frequently it is not necessary to use the straps 23 and 24 or the pouch 37 for receiving a host malleus as it has been found that a host malleus will often successfully adhere during healing to a properly placed synthetic membrane.

Referring to FIG. 8, a bone fragment 29, or a natural homograft malleus is provided in straps 23 and 24 in place of malleus 26 when a reconstruction of a host malleus is required. Bone 29 is generally cylindrical in shape and may be provided with a means, such as an aperture (not shown), in which a prosthesis may be fitted for attachment to an incus and/or stapes.

In addition to the use of a synthetic member in the restoration of a tympanic membrane, the restoration of other anatomical members is also now possible. For example, restoration of an anterior wall portion of the mastoid (posterior wall of ear canal) or other bony members is accomplished using an appropriately shaped mold of collagenous tissue within which is placed a viable autogenous filler of powdered or fragmented bone.

Figure 5:
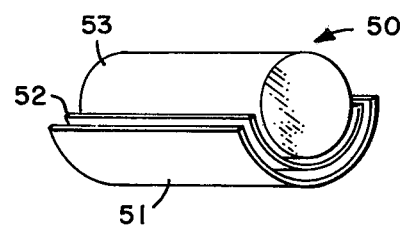

Referring to FIG. 5, there is provided, for example, a cylindrically shaped mold 50 comprising a first cylindrically shaped member or shell 51, a second shell 52 and a retaining cylinder 53. A larger section of collagenous tissue 20 is prepared as described with respect to FIG. 3, but without straps 23 and 24. A first section of tissue is laid on the concave surface of shell 51. Shell 52 is then placed over the tissue. A second section of the tissue is folded about one end of shell 52 and laid on the concave surface of shell 52. The retaining cylinder 53 is then placed on the second section of tissue and the whole assemblage secured as by a rubber O-ring. The tissue is then treated as described above with respect to the making of a synthetic tympanic membrane.

The tissue assumes and is found to retain the shape of the mold and may thereafter be surgically implanted. At the time of implantation, the two-ply piece is filled with viable autogenous bone from the recipient. The bony matrix thus formed is found to form in time a solid wall of firm bone which integrates with the adjacent host bone. Because of the performed natural shape of the implant, the surgical procedure and post-operative results are thereby enhanced.

Molds 30 and 50 are typically plastic, but may be made from a variety of non-reactive materials. It is also apparent that a variety of mold shapes may be used depending on the requirements of a particular situation. For instance, the procedures described herein may be used in the reconstruction of areas of missing dura, blood vessels and other parts of the anatomy.

The invention has been described with respect to the use of brain covering tissue and a method of preparation involving splitting of the tissue. It is to be understood, however, that in some applications, unsplit brain covering tissue and other tissue types with or without splitting may be used in practicing the present invention without departing from the scope thereof as hereinafter claimed.

What is claimed is:

1. A method of making a biosynthetic tympanic membrane and a biosynthetic tympanic membraneossicular substitute having a concave and a convex surface, comprising the steps of:
    making a mold having the shape of a natural tympanic membrane;
    preparing collagenous tissue for placement on said mold;
    placing said tissue on said mold and shaping said tissue thereon;
    treating said tissue with buffered formaldehyde, gluteraldehyde or another functionally similar fixative agent on said mold for causing said tissue to retain the external shape of said mold upon removal from said mold;
    forming a prosthetic receiving means of collagenous material on a surface of said tissue for receiving natural and prosthetic ossicle members; and
    removing said treated tissue from said mold.

2. A method according to claim 1 wherein said step of forming a prosthetic receiving means comprises forming a strap on said convex surface.

3. A method according to claim 1 wherein said step of forming a prosthetic receiving means comprises forming a pouch on said convex surface.

* * * * *